United States Patent [19]

Hammond et al.

[11] Patent Number: 5,635,626

[45] Date of Patent: Jun. 3, 1997

[54] MEASUREMENT OF A GAS CHARACTERISTIC

[75] Inventors: Paul S. Hammond, Ashby De La Zouch; Robert R. Thurston, Melbourne, both of England

[73] Assignee: British Gas plc, London, England

[21] Appl. No.: 560,647

[22] Filed: Nov. 20, 1995

[30] Foreign Application Priority Data

Dec. 2, 1994 [GB] United Kingdom ............... 9424430

[51] Int. Cl.$^6$ .............. G01N 9/00; G01N 29/02; G01N 25/22; G01F 15/04
[52] U.S. Cl. .............. 73/23.2; 73/861; 73/195; 137/79; 374/1; 374/36; 364/509
[58] Field of Search ............ 73/23.2, 861, 861.02, 73/195, 196; 137/79, 80; 374/1, 36; 364/509

[56] References Cited

U.S. PATENT DOCUMENTS

| | | | |
|---|---|---|---|
| 4,125,123 | 11/1978 | Clingman, Jr. ............... | 137/80 |
| 4,170,892 | 10/1979 | Bailitis ............... | 73/23 |
| 4,246,773 | 1/1981 | Haruta ............... | 73/24 |
| 4,345,463 | 8/1982 | Wilson et al. ............... | 73/190 CV |
| 4,384,792 | 5/1983 | Sommers et al. ............... | 374/36 |
| 4,720,196 | 1/1988 | Mondeil et al. ............... | 374/37 |
| 4,845,976 | 7/1989 | Johnson et al. ............... | 73/23 |
| 4,941,345 | 7/1990 | Altemark et al. ............... | 73/23.2 |
| 5,201,581 | 4/1993 | Vander Heyden et al. ............... | 374/36 |
| 5,237,852 | 8/1993 | Kolpak ............... | 73/23.2 |
| 5,285,675 | 2/1994 | Colgate et al. ............... | 73/23.2 |
| 5,288,149 | 2/1994 | Meyer ............... | 374/36 |
| 5,357,809 | 10/1994 | Vander Heyden ............... | 73/861.02 |

FOREIGN PATENT DOCUMENTS

| | | |
|---|---|---|
| 0 022 493 | 1/1981 | European Pat. Off. . |
| 0 242 926 | 10/1987 | European Pat. Off. . |
| 29 12 654 | 10/1979 | Germany . |
| 41 18 781 | 12/1992 | Germany . |
| WO88/00693 | 1/1988 | WIPO . |
| WO93/08457 | 4/1993 | WIPO . |

Primary Examiner—Hezron E. Williams
Assistant Examiner—J. David Wiggins
Attorney, Agent, or Firm—Oblon, Spivak, McClelland, Maier & Neustadt, P.C.

[57] ABSTRACT

Apparatus to measure the calorific value and/or the Wobbe index of fuel gas supplied along a pipe. A control can operate two outlet valves and cause an inlet valve to be locked in a closed position or be unlocked to stay in a normally open state until the gas pressure in a chamber of predetermined volume reaches a preset pressure difference above the pressure in the pipe. Under direction of the control, a pump moves fuel gas from the pipe into the chamber whilst the outlet valves are closed. Once the pressure in the chamber attains the preset difference, the inlet valve closes automatically to be held locked closed by the control. Certain properties of the gas in the chamber, such as thermal conductivity, specific heat capacity and speed of sound, are measured and corrected to STP conditions. The pump moves two samples of gas into the chamber at two sequential times, each time until the gas pressure therein attains the preset value and the inlet valve again closes automatically in a locked position. Then 1 of 2 outlet valves is opened to allow gas from the chamber to discharge to the pipe through either an orifice place or a capillary passage. This discharge allows the control to measure the gas density or viscosity at STP, from which the calorific value and/or the Wobbe index of the gas is/are determined.

17 Claims, 1 Drawing Sheet

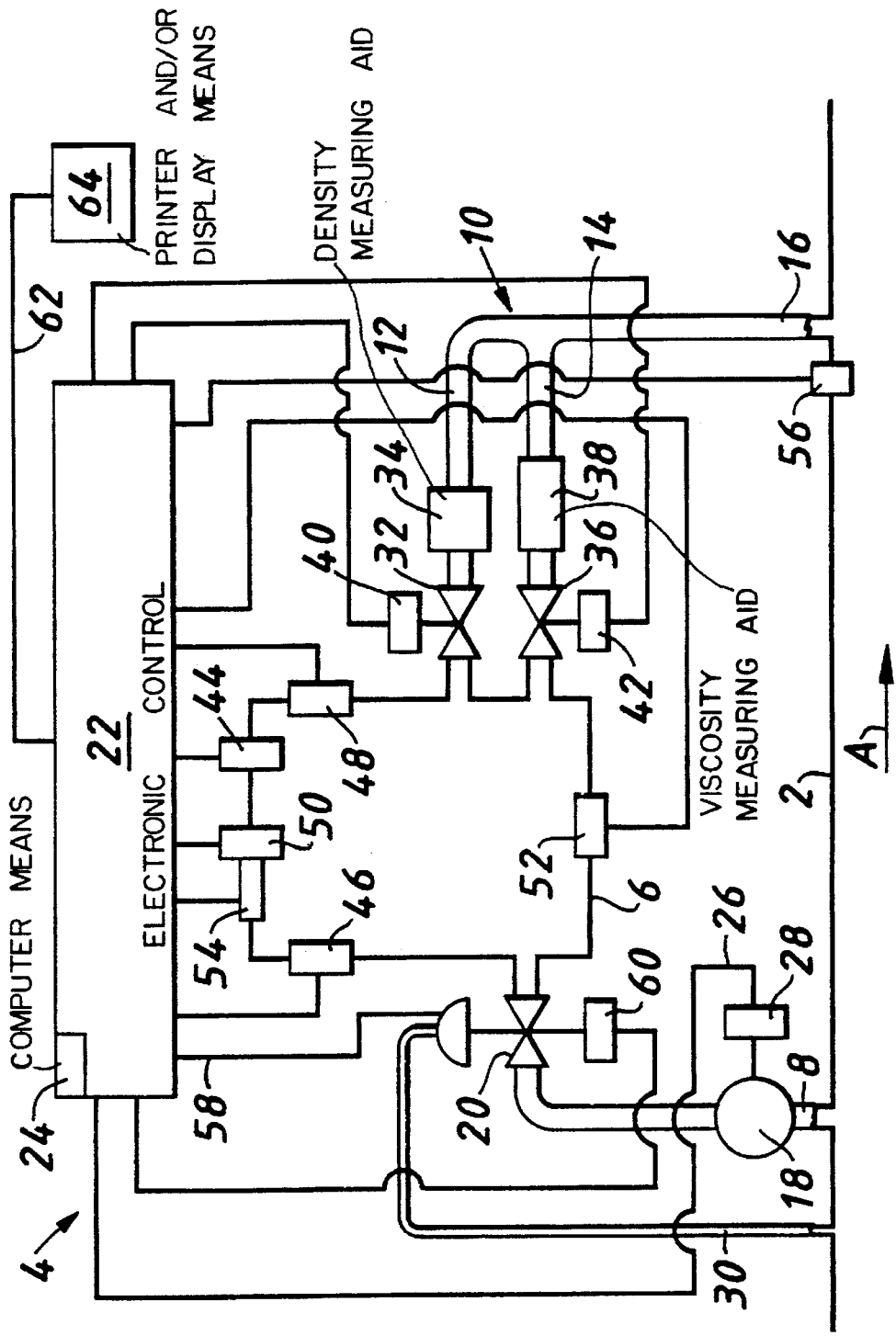

MEASUREMENT OF A GAS CHARACTERISTIC

BACKGROUND OF THE INVENTION

This invention relates to a method of measuring a gas characteristic and also to apparatus for making the measurement.

The gas characteristic(s) concerned is/are the calorific value and/or the Wobbe index of a fuel gas.

An object of the invention is to provide a means of measuring the calorific value and/or the Wobbe index of a fuel gas by physical examination of a sample of the gas from a supply of the gas, which means of measuring does not destroy the sample which may thereafter be used as useful fuel and obviates any need for and the expense of providing a venting arrangement for products of combustion because making the measurement(s) does not require combustion of the sample.

SUMMARY OF THE INVENTION

According to a first aspect of the invention there is provided a method of measuring the calorific value and/or the Wobbe index of a fuel gas comprising taking a fuel gas sample from a supply of said fuel gas and raising a predetermined volume of said sample gas to a predetermined pressure, returning said sample to the supply, making measurement of at least one of a value of the property of density or of the property of viscosity of said gas forming the sample using data obtained during the course of said return and deriving the calorific value and/or the Wobbe index by using said measured value of the density and/or of the viscosity.

According to a second aspect of the invention, there is provided an apparatus for measuring the calorific value and/or the Wobbe index of a fuel gas comprising an enclosure having a predetermined volume therewithin, pump means to deliver a sample of said fuel gas from a supply into said enclosure, delivery stopping means for stopping delivery of said gas into the enclosure when the gas therein of said predetermined volume reaches substantially a predetermined pressure, return conduit means for returning the sample gas from said enclosure to said supply, measuring means for measuring at least one of the value of the property of density or of the property of viscosity of the gas as it flows along said conduit means, and said measuring means comprising at least a part thereof disposed in said conduit means for use in the measuring of at least one of the value of said property of density or of said property of viscosity.

BRIEF DESCRIPTION OF THE DRAWING

The invention will now be further described by way of example with reference to the accompanying drawing which shows diagrammatically an apparatus formed according to the second aspect of the invention for use in carrying out the method according to the first aspect.

DETAILED DESCRIPTION OF PREFERRED EMBODIMENTS

A pipe 2 carries a supply of a fuel gas which may be at any desired pressure. Arrow A indicates the direction of gas flow. The fuel gas may be natural gas. The gas pressure may be a relatively low pressure, for example the relatively low pressure at which fuel gas is piped into industrial or domestic consumers' premises.

Apparatus to measure the calorific value and/or the Wobbe index of the fuel gas is indicated at 4. The apparatus 4 comprises an enclosure or chamber 6 of a fixed known volume connected by an inlet conduit 8 with the supply pipe 2. Leading from chamber 6 is an outlet conduit arrangement 10 comprising outlet conduits 12 and 14 merging into a conduit 16 opening into the supply pipe downstream of conduit 8. Conduit 8 comprises a pump 18 and a shutoff valve 20.

The pump 18 may be powered by any suitable means. An electronic control 22 comprising computer means 24 is connected by signal path 26 to a driver 28 connected to the pump 18 to operate or stop the latter according to instructions from the control. The valve 20 has a pilot control connected by a bleed path 30 with the supply pipe 2. Normally the valve 20 is open, but is so arranged that it is closed, by operation of the pilot control, for as long as gas pressure within the chamber 6 is substantially at a predetermined pressure difference PD greater than the gas pressure in the pipe 2.

Outlet conduit 12 comprises a shutoff valve 32 and a gas density measuring aid 34 in the form of a flow rate device, for example an orifice plate, and outlet conduit 14 comprises a shutoff valve 36 and a gas viscosity measuring aid 38 in the form of a gas flow resistance device, for example a capillary passage or tube. Each valve 32 or 34 can be opened and closed by operation of a respective driver 40 or 42 in response to signals from the control 22.

The chamber 6 includes a gas pressure sensor 44 supplying pressure information to the control 22. If it is desired to measure the speed of sound in gas within the chamber 6, the chamber can have an audible sound or ultrasound emitter 46 operated by control 22 and a receiver 48 sending sound received signals to the control, or the receiver 48 may be omitted and the device 46 may be an emitter/receiver to detect the sound signals reflected back thereto from the chamber wall facing the emitter/receiver. If it is desired to measure the thermal conductivity of gas in the chamber 6 and/or the specific heat capacity of that gas, the chamber can include temperature sensors 50 and 52 supplying temperature information to the control 22 and a heater 54 operated in response to signals from the control. A further gas pressure sensor 56 may be provided in the pipe 2 to observe the pressure of the gas supply therein and send pressure information to the control.

When the apparatus 4 is in use, the control 22 causes valves 32 and 36 to close and the pump 18 to operate thereby extracting a sample of fuel gas from the pipe 2 and pumping it into the chamber 6 until the gas pressure of the gas sample therein reaches the predetermined pressure difference PD above that of the gas in supply pipe 2, whereupon the valve 20 closes automatically and sends a signal in line 58 to the control 22 which then issues a signal to driver 60 to lock the valve 20 closed. Now the control 22 can make measurement of the value of the velocity of sound in the gas in the chamber 6, and/or of the value of its thermal conductivity and/or the value of its specific heat capacity, and making calculations that correct those measurements to what the values of velocity of sound, and/or thermal conductivity and/or specific heat capacity are at standard temperature and pressure and memorises those corrected values. Then the control 22 causes the valve 32 to open and the sample of gas under the pressure difference between that in the chamber 6 and pipe 2 returns to the pipe through conduits 12 and 16 and thus through the gas density measuring aid 34 (for example an orifice plate). The rate of gas flow through the aid 34 is a function of gas density and this is calculated by the control 22 and corrected to standard temperature and pressure and memorized in the control. (The control 22 may measure the value of the rate of decay of the gas pressure in the chamber 6 of fixed volume, and from that decay rate value calculate the value of the gas density). Now the control 22 causes the valve 32 to close and the driver 60 to unlock the valve 20 so that it automatically opens thereby allowing a further sample of make-up gas to be pumped into the chamber 6 until the valve 20 automatically closes again on the pressure in the chamber attaining the predetermined pressure difference PD above the pressure in pipe 2. The signal on line 58 again causes the control 22 to operate the driver 60 to lock the valve 20 closed and the control also operates the driver 28 to stop the pump 18. The control 22 operates the driver 42 which opens valve 36 and allows the gas sample to pass from the chamber 6 back to the pipe 2 through conduits 14 and 16. In doing so the gas passes through the gas viscosity measuring aid 38 (for example a capillary passage or tube). The control 22 observes the decay, which is a function of the gas viscosity, of the gas pressure in the chamber 6 and fits the observed substantially exponential form of the decay against data stored in the control 22 to give a value for the gas viscosity corrected to standard temperature and pressure. That value is memorized in the control. The control 22 operates the drivers 40 and 60 to open the valve 32 and unlock the valve 20 so it can open automatically.

Stored in the control 22 are different sets of predetermined reference data for a given fuel gas, each set of data comprising a gas density value, a gas viscosity value, a speed of sound in gas value, and/or a gas thermal conductivity value and/or a gas specific heat capacity value all corrected to standard temperature and pressure, and each see correlated to a particular calorific value and/or Wobbe index. The measured values of the gas density, viscosity, and/or speed of sound, and/or thermal conductivity and/or specific heat capacity obtained by the apparatus 4 are fitted by the control 22 against the reference sets until a reference set is discovered having values corresponding the most closely to the measured values.

The inference is drawn by the control 22 that the calorific value and/or Wobbe index correlated to that reference set are/is the calorific value and/or Wobbe index of the fuel gas in the pipe 2, and the control 22 sends a signal on information path 62 conveying the inferred calorific value and/or Wobbe index which may be sent to some remote location and/or may be visually represented by means of appropriate informational apparatus 64, for example printer means and/or visual display unit means. The signal on path 62 may be sent to a gas volumetric metering means measuring the amount of gas or potential heat energy supplied and/or computing the monetary value of the gas supplied.

If desired the bleed path 30 may be omitted and the shutoff valve 20 substituted by another shutoff valve operated wholly in response to signals from the control 22 which, upon receiving signals from the pressure sensors 44 and 56, can observe when the gas pressure in the chamber 6 is the predetermined pressure difference PD above the gas pressure in the supply pipe 2, whereupon the said substitute shutoff valve is closed in response to a signal from the control 22 and held closed until it is opened in response to a signal from the control when it is next desired to charge the chamber 6 with another sample of the gas.

We claim:

1. A combustionless method of measuring the calorific value and/or the Wobbe index of a fuel gas comprises taking a fuel gas sample from a supply of said fuel gas and raising a predetermined volume of said sample gas to a predetermined pressure, returning said sample to the supply, making measurement of at least one of a value of the property of density or of the property of viscosity of said gas forming the sample using data obtained during the course of said return and deriving the calorific value and/or the Wobbe index by using said measured value of the density and/or of the viscosity, and wherein a said measured value of at least one of said properties is compared with a plurality of prederived values of the property each correlated to a particular respective calorific value and/or to a particular respective Wobbe index, whereby from said comparison substantially the calorific value and/or Wobbe index of the fuel gas can be inferred.

2. A method as claimed in claim 1, wherein the gas sample is returned to said supply under effect of a pressure difference between said predetermined pressure and said supply.

3. A method as claimed in claim 1, in wherein whilst said sample is at substantially said predetermined pressure measurement is made of at least one of the value of the property of speed of sound in the gas forming said sample, the value of the property of thermal conductivity of the gas forming said sample and the value of the property of specific heat capacity of the gas forming said sample, and said measured value or values of one or more of said speed of sound and/or of said thermal conductivity and/or of said specific heat is/are used to derive said calorific value and/or Wobbe index.

4. A method as claimed in claim 3, wherein said measured value of each of two or more of said properties is compared with a plurality of prederived values of the two or more properties, there are groups of prederived values of said properties each group comprising at least two prederived values, each value corresponding to a respective different said property within the particular group and each group of said prederived values is correlated to a particular respective calorific value and/or to a particular respective Wobbe index, whereby from said comparison substantially the calorific value and/or the Wobbe index of the fuel gas can be inferred.

5. A method as claimed in claim 1, wherein making a measurement of the property of density of the gas comprises returning the gas through an orifice plate.

6. A method as claimed in claim 1, wherein making a measurement of the property of viscosity of the gas comprises returning the gas through a capillary passage.

7. A method as claimed in claim 1, wherein two successive said predetermined volumes of said gas are raised to said predetermined pressure, and a measurement of the value of one of the properties of density or viscosity is made using data obtained during the course of returning one of said volumes of gas to the supply and a measurement of the value of the other of said properties of density or viscosity is made using data obtained during the course of returning the other of said volumes to said supply.

8. A test apparatus for measuring the calorific value and or the Wobbe index of a fuel gas without loss or consumption of a fuel gas sample under test comprising an enclosure having a predetermined volume therewithin, pump means for delivering a sample of said fuel gas from a supply into said enclosure, delivery stopping means for stopping delivery of said gas into the enclosure when the gas therein of said predetermined volume reaches substantially a predetermined pressure, return conduit means for returning the sample gas from said enclosure to said supply, measuring means for measuring at least one of a value of the property of density or the property of viscosity of the gas as it flows along said conduit means, said measuring means comprising at least a part thereof disposed in said conduit means for use in the measuring of at least one of the value of said property of density or of said property of viscosity, another part of said measuring means comprising control means, said enclosure being provided with gas pressure sensing means and temperature sensing means, and the gas pressure sensing means and the temperature sensing means being connected to said control means arranged for calculating a value of the property of density of the gas corrected to standard temperature and pressure and/or for calculating a value of the property of viscosity of the gas corrected to standard temperature and pressure, said control means comprising means for comparing the measured value of at least one of said properties with a plurality of prederived values of the property stored in said control means, each of said prederived values of the property being correlated to a particular Wobbe index, and for inferring from said comparison substantially the calorific value and/or Wobbe index of the fuel gas.

9. Apparatus as claimed in claim 8, wherein said predetermined pressure is the pressure which is greater than the pressure of the gas supply by substantially a predetermined pressure difference.

10. Apparatus as claimed in claim 8, wherein a first conduit for returning the gas sample to the supply comprises a first part for use in measuring the value of the property of density of the gas and first valve means between the enclosure and the said first part, and a second conduit for returning the gas sample to the supply comprises a second part for use in measuring the value of the property of viscosity of the gas and second valve means between said enclosure and the said second part.

11. Apparatus as claimed in claim 8, wherein a said part for use in measuring the value of the property of density of the gas is an orifice plate.

12. Apparatus as claimed in claim 8, wherein a said part for use in measuring the value of the property of viscosity of the gas is a capillary passage.

13. Apparatus as claimed in claim 8, wherein an inlet conduit for passage of the gas sample between the supply and the enclosure comprises said pump means and valve means between the pump means and said enclosure.

14. Apparatus as claimed in claim 10, arranged for a sample of the gas raised to said predetermined pressure in the enclosure to discharge through one of the first conduit or the second conduit for return to said supply and for another sample of the gas raised to said predetermined pressure in said enclosure to discharge through the remaining other of said first conduit or said second conduit to the supply.

15. Apparatus as claimed in claim 9, wherein the enclosure is provided with means to emit and receive sound connected to said control means arranged for calculating a value of the property of the speed of sound in the gas in the enclosure corrected to standard temperature and pressure, and/or the enclosure is provided with means connected to the control means whereby said control means can calculate a value of the property of thermal conductivity of the gas in the enclosure corrected to standard temperature and pressure and/or the value of the specific heat of the gas in the enclosure corrected to standard temperature and pressure.

16. Apparatus as claimed in claim 8, wherein which said control means is arranged for comparing the measured value of each of two or more of said properties with a plurality of prederived values of the properties stored in the control means, said control means having stored therein groups of prederived values of said properties each group comprising at least two prederived values each corresponding to a respective different said property and each group of said prederived values being correlated to a particular respective calorific value and/or to a particular respective Wobbe index, and the control means being arranged for inferring from said comparison substantially the calorific value and/or Wobbe index of the fuel gas.

17. Apparatus as claimed in claim 10, further comprising control means, said enclosure being provided with gas pressure sensing means and temperature sensing means, the gas pressure sensing means and the temperature sensing means being connected to said control means arranged for calculating a value of the property of density of the gas corrected to standard temperature and pressure and/or for calculating a value of the property of viscosity of the gas corrected to standard temperature and pressure, and said control means being arranged for controlling the first valve means and second valve means and/or the pump means.

* * * * *